United States Patent
Nakamura

(10) Patent No.: US 10,138,548 B2
(45) Date of Patent: Nov. 27, 2018

(54) FILM THICKNESS MEASURING DEVICE, POLISHING APPARATUS, FILM THICKNESS MEASURING METHOD AND POLISHING METHOD

(71) Applicant: EBARA CORPORATION, Tokyo (JP)

(72) Inventor: Akira Nakamura, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 12 days.

(21) Appl. No.: 15/647,684

(22) Filed: Jul. 12, 2017

(65) Prior Publication Data

US 2018/0016676 A1   Jan. 18, 2018

(30) Foreign Application Priority Data

Jul. 13, 2016  (JP) .................................. 2016-138434

(51) Int. Cl.
| | |
|---|---|
| B24B 37/013 | (2012.01) |
| C23C 14/54 | (2006.01) |
| G01N 27/02 | (2006.01) |
| B24B 37/00 | (2012.01) |
| B24B 37/10 | (2012.01) |
| B24B 49/04 | (2006.01) |
| B24B 49/10 | (2006.01) |

(52) U.S. Cl.
CPC ............ *C23C 14/542* (2013.01); *B24B 37/00* (2013.01); *B24B 37/013* (2013.01); *B24B 37/107* (2013.01); *B24B 49/04* (2013.01); *B24B 49/105* (2013.01); *G01N 27/025* (2013.01)

(58) Field of Classification Search
CPC ..... C23C 14/542; B24B 37/00; B24B 37/013; B24B 37/107; B24B 49/04; B24B 49/105
USPC .................................. 451/5, 6, 41, 285-290
See application file for complete search history.

(56) References Cited

U.S. PATENT DOCUMENTS

| | | | |
|---|---|---|---|
| 6,276,987 B1 * | 8/2001 | Li ......................... | B24B 37/013 451/287 |
| 6,290,572 B1 * | 9/2001 | Hofmann .............. | B24B 37/013 451/287 |
| 6,322,422 B1 * | 11/2001 | Satou .................... | B24B 37/005 451/283 |
| 6,432,728 B1 * | 8/2002 | Tai ........................ | B24B 37/013 257/E21.244 |
| 6,609,947 B1 * | 8/2003 | Moore .................. | B24B 37/013 451/287 |

(Continued)

FOREIGN PATENT DOCUMENTS

| | | |
|---|---|---|
| JP | 2005-121616 A | 5/2005 |
| JP | 2016-138434 A | 8/2016 |

*Primary Examiner* — George Nguyen
(74) *Attorney, Agent, or Firm* — Baker & Hostetler LLP

(57) ABSTRACT

Eddy current formable in a polishing target is detected as an impedance by an eddy current sensor. A resistance component and a reactance component of the impedance are associated with respective axes of a coordinate system having orthogonal axes, respectively. An angle calculator calculates the tangent of an intersection angle between a first straight line connecting a first point corresponding to an impedance for a zero film thickness, and a second point corresponding to an impedance for a non-zero film thickness, and a diameter of a circle passing through the first point. A film thickness calculator determines the film thickness from the tangent.

9 Claims, 10 Drawing Sheets

(56) References Cited

U.S. PATENT DOCUMENTS

| | | | | |
|---|---|---|---|---|
| 6,876,454 B1* | 4/2005 | Birang | ................. | B24B 37/013 356/503 |
| 2003/0008600 A1* | 1/2003 | Ide | ....................... | B24B 37/013 451/41 |
| 2004/0111175 A1* | 6/2004 | Kim | .................... | B24B 37/013 700/121 |
| 2005/0142991 A1* | 6/2005 | Nakao | ................... | B24B 37/013 451/64 |
| 2005/0191858 A1* | 9/2005 | Fukunaga | ............. | B24B 37/013 438/691 |
| 2008/0071414 A1* | 3/2008 | Fujita | ................... | B24B 37/013 700/121 |
| 2008/0139087 A1* | 6/2008 | Togawa | ............... | B24B 37/013 451/8 |
| 2012/0276814 A1* | 11/2012 | Zhang | ................. | B24B 37/013 451/5 |
| 2013/0211765 A1* | 8/2013 | Lu | ....................... | B24B 37/013 702/97 |

\* cited by examiner

FILM THICKNESS MEASURING DEVICE, POLISHING APPARATUS, FILM THICKNESS MEASURING METHOD AND POLISHING METHOD

CROSS-REFERENCE TO RELATED APPLICATION

This application is based upon and claims benefit of priority from Japanese Patent Application No. 2016-138434 filed on Jul. 13, 2016, the entire contents of which are incorporated herein by reference.

BACKGROUND OF THE INVENTION

Field of the Invention

The present invention relates to a film thickness measuring device, a polishing apparatus, a film thickness measuring method and a polishing method.

Description of the Related Art

Recently, in connection with higher integration and higher density of semiconductor devices, wiring of circuits has been increasingly finer, and the number of layers of multilayered wiring has also increased. In order to realize the multilayered wiring while miniaturizing circuits, the surfaces of semiconductor devices are required to be precisely flattened.

Chemical Mechanical Polishing (CMP) has been known as a flattening technique for flattening the surfaces of semiconductor devices. A polishing apparatus for performing CMP includes a polishing table to which a polishing pad is fitted, and a top ring for holding a polishing target (a substrate such as a semiconductor wafer, or each kind of film formed on the surface of a substrate). The polishing apparatus polishes the polishing target held on the top ring by pressing the polishing target against the polishing pad while rotating the polishing table.

The polishing apparatus includes a film thickness measuring device for detecting an end point of a polishing process based on the film thickness of a polishing target. The film thickness measuring device has a film thickness sensor for detecting the film thickness of the polishing target. An eddy current sensor is representative of the film thickness sensor.

The eddy current sensor is arranged in a cavity formed on the polishing table, and detects the film thickness of the polishing target when the eddy current sensor is facing the polishing target while rotating along with the rotation of the polishing table. The eddy current sensor causes the polishing target such as a conductive film or the like to induce eddy current, and detects variation of the thickness of the polishing target based on variation of magnetic field occurring due to the eddy current induced in the polishing target.

Japanese Patent Laid-Open No. 2005-121616 discloses a technique on the eddy current sensor. The eddy current sensor includes a sensor coil arranged in the neighborhood of the conductive film, a signal source for supplying an AC signal to the sensor coil to form eddy current in the conductive film, and a detection circuit for detecting the eddy current formed in the conductive film as an impedance when viewed from the sensor coil. A resistance component and a reactance component of the impedance are displayed on the orthogonal coordinate axes. The film thickness of the conductive film is detected from the intersection angular degree between lines connecting the coordinate of the impedance and the coordinate of a specified center point.

According to a method of determining the film thickness from the angular degree, the relationship between the angular degree and the film thickness as shown in FIG. 13 of the foregoing publication is measured in advance, and an angular degree is directly converted to a film thickness by using this relationship. Specifically, a center point (reference point) P corresponding to the film quality of the conductive film and multiple elevation angles θ associated with multiple film thicknesses of the conductive film are obtained and stored in a memory. A preliminary measurement straight line is obtained for each elevation angle θ. Multiple preliminary measurement lines are obtained according to the multiple elevation angles θ. Thereafter, when the substrate polishing apparatus is actuated, the film thickness of the conductive film is calculated based on the elevation angle θ of an actual measurement straight line rn connecting the output values of the resistance component and the reactance component of an impedance for each measurement and the center point P in the memory, and the preliminary measurement straight line.

In Japanese Patent Laid-Open No. 2005-121616, a reference point P and multiple preliminary measurement straight lines required to calculate the film thickness of a conductive film based on an elevation angle θ are determined through multiple measurements in advance. That is, various film thicknesses and impedances associated with the distances between various kinds of polishing targets and an eddy current sensor are measured in advance. Accordingly, this method has a problem that the frequency of measurements to be performed in advance is large.

The present invention has been implemented to solve the foregoing problem, and has an object to provide a film thickness measuring device, a polishing apparatus, a film thickness measuring method and a polishing method that can reduce the frequency of film thickness measurements to be performed in advance as compared with the prior art.

SUMMARY OF THE INVENTION

In order to attain the above object, according to a first aspect of the present invention, there is provided a film thickness measuring device for measuring a film thickness of a polishing target wherein when eddy current formable in the polishing target is detected as an impedance by an eddy current sensor, the film thickness measuring device receives an input of the impedance and determines the film thickness from the input impedance, wherein when respective axes of a coordinate system having two orthogonal coordinate axes are associated with a resistance component and a reactance component of the impedance respectively, a point on the coordinate system which corresponds to the impedance forms at least a part of a circle, and wherein the film thickness measuring device comprises: an angle calculator that calculates a tangent or angular degree of an intersection angle between a first straight line connecting a first point corresponding to the impedance for a film thickness of zero and a second point corresponding to the impedance for a non-zero film thickness and a diameter of the circle which passes through the first point; and a film thickness calculator that determines the film thickness from the tangent or the angular degree.

In this embodiment, the tangent or angular degree of the angle is calculated, and the film thickness is determined from the tangent or the angular degree. In this embodiment, it is unnecessary to perform multiple measurements in advance as in the case of the prior art. There is an advantage that variation of the measurement value due to variation of the thickness of the polishing pad can be considered by merely determining only the first point for the film thickness of zero with respect to the thickness of one type polishing pad.

The reason for this is as follows. The second point can be determined during the measurement of the film thickness. The center of a circle to which the second point concerned belongs is determined from information (coordinate values) of plural second points. Information on the diameter of the circle (the equation of the diameter (straight line) or the length of the diameter) can be calculated from the information (coordinate value) on the center of the circle and the information (coordinate value) on the first point (or the second point). That is, the information required in advance is only the information on the first point, and the information on the second point and the diameter of the circle can be achieved during the measurement of the film thickness. Various methods of determining the center of a circle or the diameter of a circle will be described in detail later.

According to a second aspect, the film thickness measuring device is configured to have a first storage unit capable of storing a center position of the circle that can be calculated from a plurality of the second points located on the circle and obtained by the eddy current sensor, wherein the angle calculator calculates the tangent or the angular degree from the stored center position of the circle, the first point and the second points obtained by the eddy current sensor after the center position of the circle is calculated.

According to a third aspect, the film thickness measuring device is configured so that points on the coordinate system that correspond to impedances obtained for different distances between the polishing target and the eddy current sensor form different circles, center of each of the different circles being located on a second straight line, and wherein the film thickness measuring device further comprises a second storage unit capable of storing information on the second straight line, and the angle calculator determines that a point which is located on the stored second straight line and at which a distance from the first point and a distance from the second point are equal to each other is a center of the circle to which the second point belongs, and calculates the tangent or the angular degree from the position of the center of the circle, the first point and the second point.

According to a fourth aspect, the film thickness measuring device is configured so that points on the coordinate system that correspond to impedances obtained for different distances between the polishing target and the eddy current sensor form the different circles, center of each of the different circles being located on a second straight line and the first point being located on the second straight line, and wherein the film thickness measuring device has a second storage unit capable of storing information on the second straight line, and the angle calculator calculates the tangent or the angular degree while the angular degree of an intersection angle between the stored second straight line and the first straight line is set as the angular degree of the intersection angle between the first straight line and the diameter of the circle that passes through the first point.

According to a fifth aspect, the film thickness measuring device is configured so as to further comprise a straight line calculator that calculates information on the second straight line and so that with respect to each of the at least two circles corresponding to different distances between the polishing target and the eddy current sensor, the straight line calculator calculates a center of each of the circles from at least three points on the circle, and outputs information on a straight line connecting the calculated centers of the at least two circles as information on the second straight line to the second storage unit, and the second storage unit stores the input information on the second straight line.

According to a sixth aspect, the film thickness measuring device is configured so that points on the coordinate system that correspond to impedances obtained for different distances between the polishing target and the eddy current sensor form the different circles, and the first point is a point common to the different circles, and wherein the film thickness measuring device has a straight line calculator that calculates information on the second straight line, with respect to one of the circles, the straight line calculator calculates a center of the circle from at least three points on the circle, and outputs information of a straight line connecting the calculated center of the circle and the first point as information on the second straight line to the second storage unit, and the second storage unit stores the input information on the second straight line.

According to a seventh aspect, there is provided a polishing apparatus for polishing a polishing target that comprises: a polishing unit that polishes the polishing target; an eddy current sensor that forms eddy current in the polishing target and detect the formed eddy current to measure a film thickness of the polishing target; a receiver for outputting the detected eddy current as an impedance; and the film thickness measuring device according to any one of the first to sixth aspects that receives an input of the impedance and determines the film thickness from the input impedance.

According to an eighth aspect, there is provided a film thickness measuring method for measuring a film thickness of a polishing target by, when eddy current formable in the polishing target is detected as an impedance by an eddy current sensor, receiving an input of the impedance and determining the film thickness from the input impedance, wherein when respective axes of a coordinate system having two orthogonal coordinate axes are associated with a resistance component and a reactance component of the impedance respectively, a point on the coordinate system which corresponds to the impedance forms at least a part of a circle, and wherein the film thickness measuring method comprises: a step of calculating a tangent or angular degree of an intersection angle between a first straight line connecting a first point corresponding to the impedance for a film thickness of zero and a second point corresponding to the impedance for a non-zero film thickness and a diameter of the circle which passes through the first point; and a step of determining the film thickness from the tangent or the angular degree.

According to a ninth aspect, there is provided a polishing method for polishing a polishing target that comprises: a polishing step of polishing the polishing target; a step of forming eddy current in the polishing target and detecting the formed eddy current to measure a film thickness of the polishing target; a step of outputting the detected eddy current as an impedance; and a film thickness measuring step of receiving an input of the impedance and determining the film thickness from the input impedance, wherein when respective axes of a coordinate system having two orthogonal coordinate axes are associated with a resistance component and a reactance component of the impedance respectively, a point on the coordinate system which corresponds to the impedance forms at least a part of a circle, and wherein the film thickness measuring step comprises: a step of calculating a tangent or angular degree of an intersection angle between a first straight line connecting a first point corresponding to an impedance for the film thickness of zero and a second point corresponding to the impedance for a non-zero film thickness and a diameter of the circle which passes through the first point; and a step of determining the film thickness from the tangent or the angular degree.

DETAILED DESCRIPTION OF THE PREFERRED EMBODIMENTS

Figure 1:
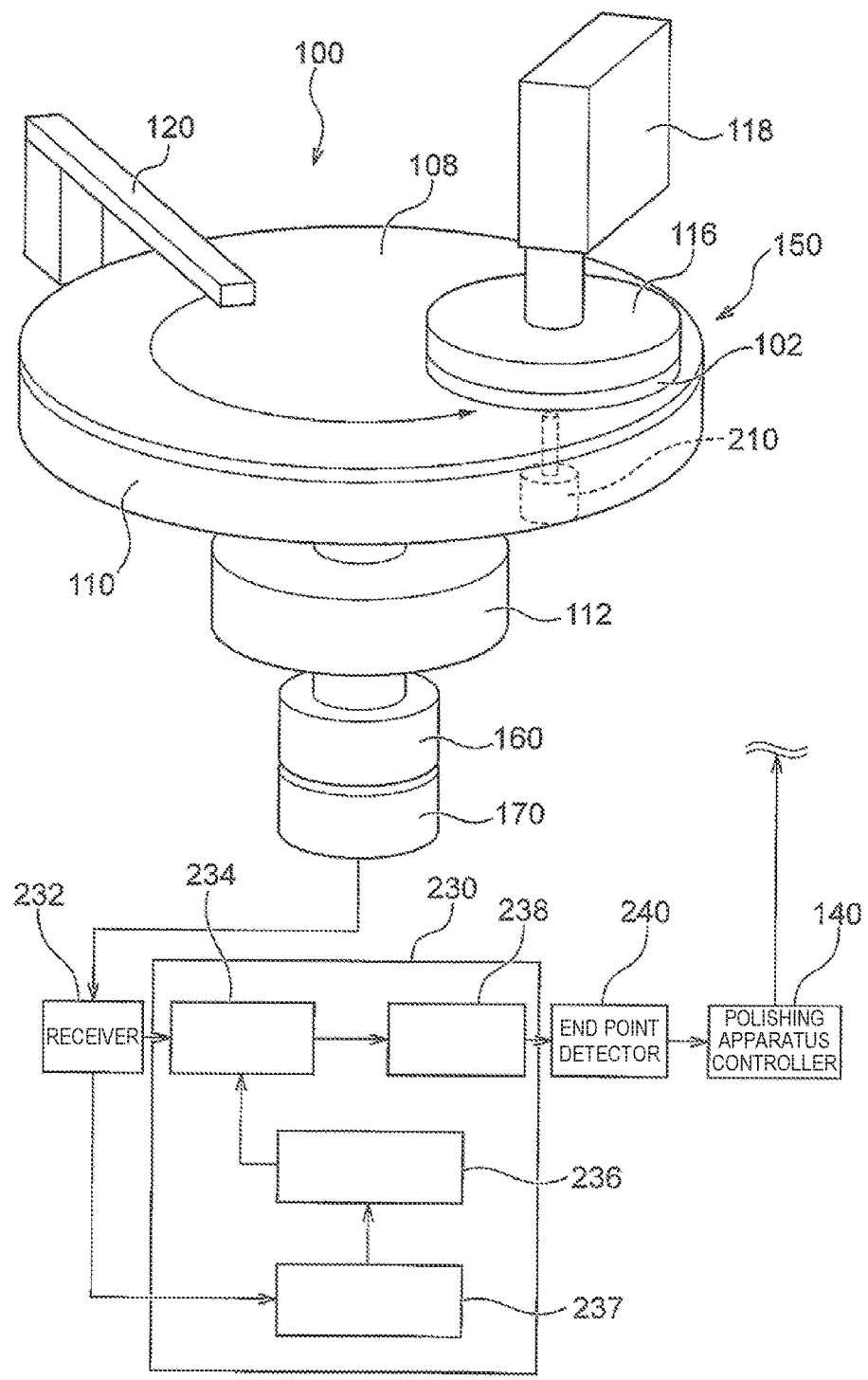
FIG. 1 is a diagram schematically showing the overall configuration of a polishing apparatus.

Embodiments according to the present invention will be described hereunder with reference to the drawings. In the following embodiments, the same or corresponding members are represented by the same reference numerals, and the duplicative descriptions thereof are eliminated.

FIG. 1 is a diagram schematically showing the overall configuration of a polishing apparatus according to an embodiment of the present invention. As shown in FIG. 1, a polishing apparatus 100 includes a polishing unit 150 for polishing a polishing target (for example, a substrate such as a semiconductor wafer, or each kind of film formed on the surface of a substrate) 102. The polishing unit 150 includes a polishing table 110 having a top surface to which a polishing pad 108 for polishing the polishing target 102 may be fitted, a first electric motor 112 for rotating the polishing table 110, a top ring 116 capable of holding the polishing target 102, and a second electric motor 118 for rotating the top ring 116.

The polishing unit 150 has a slurry line 120 for supplying polishing abrasive liquid containing polishing material onto the top surface of the polishing pad 108. The polishing apparatus 100 has a polishing apparatus controller 140 for outputting various kinds of control signals associated with the polishing unit 150.

The polishing apparatus 100 has an eddy current sensor 210 which is arranged in a cavity formed on the polishing table 110, and detects the film thickness of the polishing target 102 along a polishing surface while following the rotation of the polishing table 110.

When the polishing target 102 is polished, the polishing apparatus 100 supplies polishing slurry containing polishing abrasive particles from the slurry line 120 onto the top surface of the polishing pad 108, and rotates the polishing table 110 by the first electric motor 112. Then, the polishing apparatus 100 presses the polishing target 102 held on the top ring 116 against the polishing pad 108 while rotating the top ring 116 around a rotational axis which is eccentrically displaced from the rotational axis of the polishing table 110. As a result, the polishing target 102 is polished and flattened by the polishing pad 108 holding the polishing slurry.

A receiver 232 is connected to the eddy current sensor 210 through rotary joint connectors 160, 170. The receiver 232 receives a signal output from the eddy current sensor 210, and outputs the signal as an impedance.

As shown in FIG. 1, a film thickness measuring device 230 performs predetermined signal processing on the impedance output from the receiver 232, and outputs the processing result to an end point detector 240.

The end point detector 240 monitors variation of the film thickness of the polishing target 102 based on the signal output from the film thickness measuring device 230. The end point detector 240 is connected to the polishing apparatus controller 140 for performing various kinds of control associated with the polishing apparatus 100. When detecting a polishing end point of the polishing target 102, the end point detector 240 outputs a signal indicating the detection of the polishing end point to the polishing apparatus controller 140. Upon reception of the signal indicating the polishing end point from the end point detector 240, the polishing apparatus controller 140 controls the polishing apparatus 100 to finish the polishing operation. During the polishing operation, the polishing apparatus controller 140 controls the press force of the polishing target 102 based on corrected film thickness data.

Figure 2:
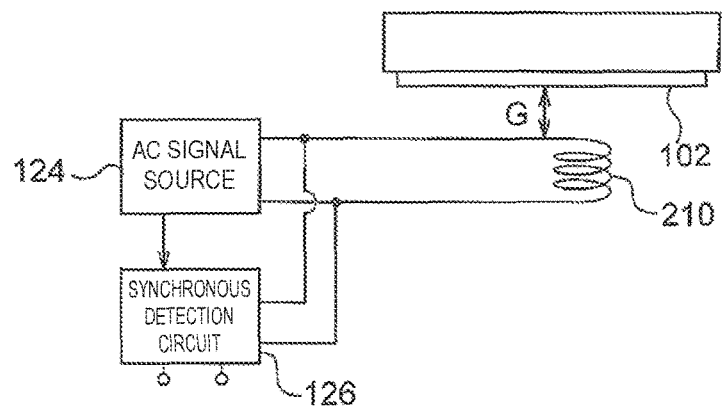
FIG. 2 is a block diagram showing an exemplary configuration of an eddy current sensor for measuring an impedance.

FIG. 2 shows the eddy current sensor 210 equipped to the polishing apparatus 100. An impedance when the conductive film side is viewed from the sensor coil varies, and the eddy current sensor detects the film thickness based on the variation of the impedance. In the eddy current sensor 210, the sensor coil is arranged in the neighborhood of the polishing target 102 as a detection target, and an AC signal source 124 is connected to the sensor coil. Here, the polishing target 102 as the detection target is, for example, a copper-plated film (a deposition film of metal material such as Au, Cr or W may be used) having a thickness of about 0 to 2 μm formed on a semiconductor wafer W. The sensor coil is arranged in the neighborhood of the conductive film as the detection target, for example so as to be spaced from the conductive film as the detection target by about 0.5 to 5 mm. The synchronous detection circuit 126 detects an impedance Z containing the polishing target 102 as the detection target when viewed from the sensor coil side (will be described in detail later).

Figure 3:
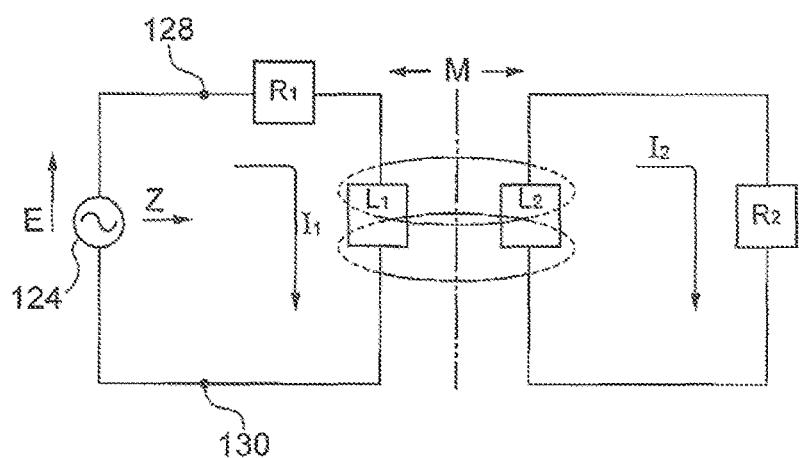
FIG. 3 is an equivalent circuit diagram of the block diagram of FIG. 2.

In an equivalent circuit shown in FIG. 3, the oscillation frequency of the AC signal source 124 is fixed, and when the film thickness of the polishing target 102 varies, the impedance Z when the sensor coil side is viewed from the AC signal source 124 varies. That is, in the equivalent circuit shown in FIG. 3, eddy current $I_2$ flowing in the polishing target 102 is determined by equivalent resistance $R_2$ and self-inductance $L_2$ of the polishing target 102. When the film thickness varies, the eddy current $I_2$ varies, and through a mutual inductance M with the sensor coil side, the variation of the eddy current is captured as variation of the impedance Z when viewed from the AC signal source 124 side. Here, $L_1$ represents a self-inductance component of the sensor coil, and $R_1$ represents a resistance component of the sensor coil.

The eddy current sensor will be specifically described hereunder. The AC signal source 124 is an oscillator having a fixed frequency of about 1 to 50 MHz, and for example a quartz oscillator is used. Current $I_1$ is made to flow in the sensor coil with an AC voltage supplied to the AC signal source 124. Current flows through the coil arranged in the neighborhood of the polishing target 102, whereby a resulting magnetic flux crosses the polishing target 102, and the mutual inductance M is formed between the coil and the polishing target 102, so that eddy current $I_2$ flows in the polishing target 102. Here, $R_1$ represents the equivalent resistance on the primary side containing the sensor coil, and $L_1$ likewise represents the self-inductance on the primary side containing the sensor coil. On the polishing target 102 side, $R_2$ represents the equivalent resistance equivalent to an eddy current loss, and $L_2$ represents the self-inductance thereof. The impedance Z when the sensor coil side is viewed from terminals 128, 130 of the AC signal source 124 varies according to the magnitude of the eddy current loss formed in the polishing target 102.

Figure 4:
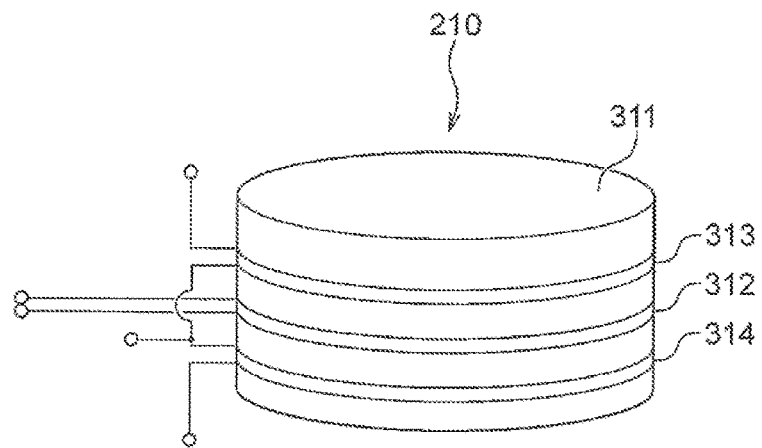
FIG. 4 is a perspective view showing an exemplary configuration of a sensor coil of the eddy current sensor.

FIG. 4 shows an exemplary configuration of the sensor coil in the eddy current sensor according to this embodiment. The sensor coil is configured to be separated into a coil for forming eddy current in the conductive film and a coil for detecting the eddy current of the conductive film, and comprises coils of three layers wound around a bobbin 311. An exciting coil 312 at the center is an exciting coil connected to the AC signal source 124. The exciting coil 312 forms eddy current in the polishing target 102 on the semiconductor wafer W arranged in the neighborhood of the exciting coil 312 with magnetic field which is formed by a voltage supplied from the AC signal source 124 to the exciting coil 312. A detection coil 313 is arranged on the upper side (conductive film side) of the bobbin 311, and detects magnetic field generated by the eddy current formed in the conducive film. A balance coil 314 is arranged on the opposite side to the detection coil 313 of the exciting coil 312.

Figure 5:
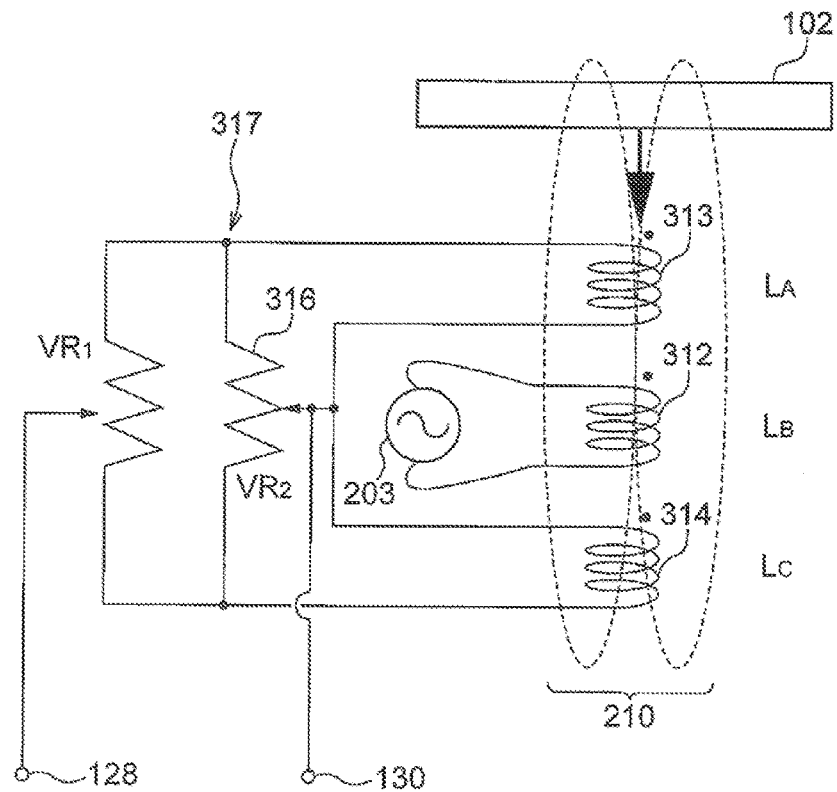
FIG. 5 is a circuit diagram showing a connection example of the sensor coil of FIG. 4.

FIG. 5 shows a connection example of the respective coils. The detection coil 313 and the balance coil 314 constitute a reverse-phase series circuit as described above, and both the ends of the reverse-phase series circuit are connected to a resistance bridge circuit 317 containing a variable resistor 316. The coil 312 is connected to the AC signal source 203, and generates an alternating magnetic flux to form eddy current in a conductive film 201' arranged in the neighborhood of the coil 312. By adjusting the resistance values of variable resistors $VR_1$, $VR_2$, the output voltage of the series circuit comprising the coils 313 and 314 is adjustable to be equal to zero when no conductive film exits.

Figure 6:
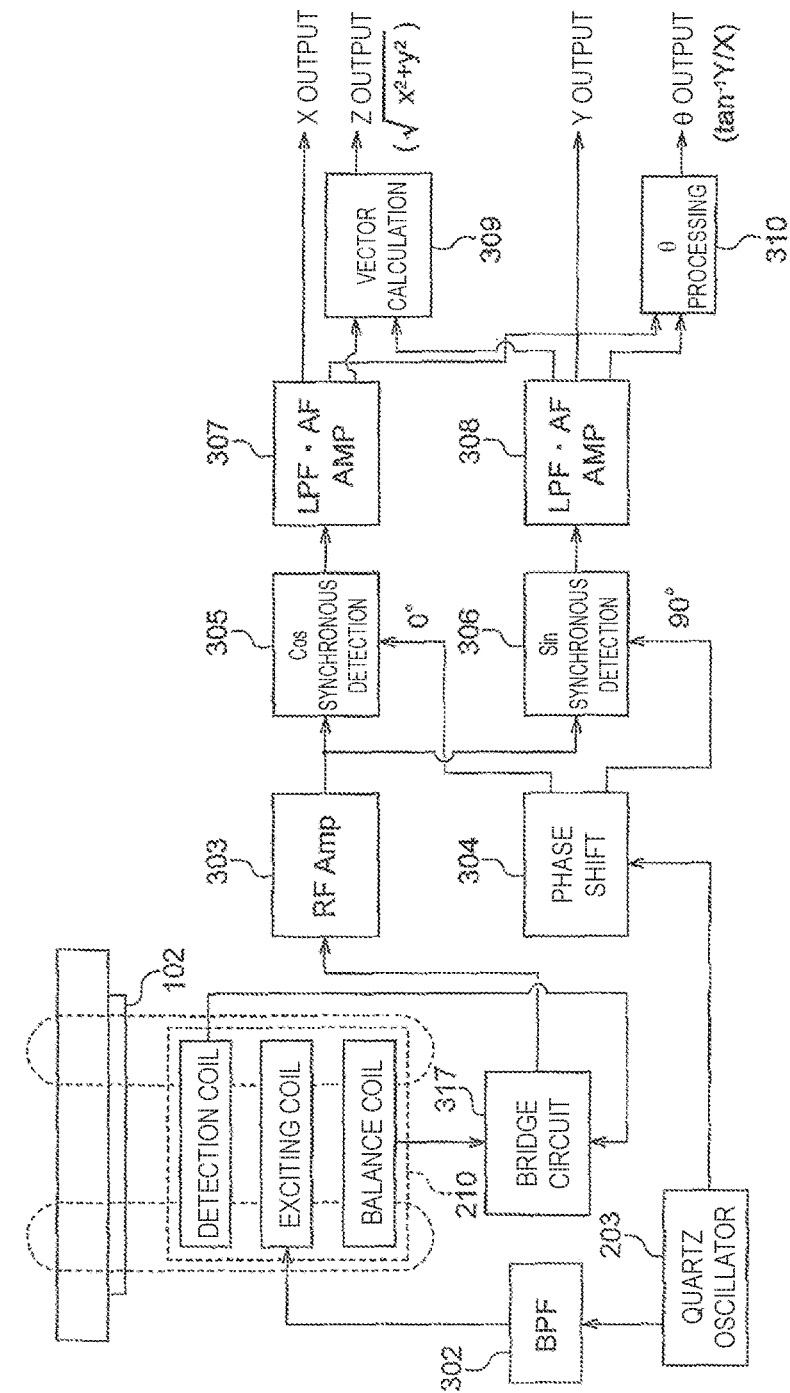
FIG. 6 is a block diagram showing a synchronous detection circuit for a sensor coil output.

FIG. 6 shows an exemplary measurement circuit of the impedance Z when the sensor coil 202 side is viewed from the AC signal source 203 side. The measurement circuit for the impedance Z shown in FIG. 6 can take out an impedance flat plane coordinate value (X, Y) (that is, the reactance component (Y), the resistance component (X)), an impedance (Z=X+iY) and a phase output ($\theta=\tan^{-1}Y/X$) which are conformed with variation of the film thickness. Accordingly, by using these signal outputs, it is possible to detect the progress status in a more variety of aspects like a case where the film thickness is measured based on the magnitude of various kinds of components of the impedance, for example.

As described above, the signal source 203 for supplying an AC signal to the sensor coil arranged in the neighborhood of the semiconductor wafer W on which the polishing target 102 as the detection target is formed is an oscillator having a fixed frequency which comprises a quartz oscillator. The AC signal source 203 supplies a voltage having a fixed frequency ranging from 1 to 50 MHz, for example. The AC voltage formed by the signal source 203 is supplied to the exciting coil 312 via a bandpass filter 302. Signals detected at the terminals 128, 130 of the sensor coil are input to a synchronous detector comprising a cos synchronous detection circuit 305 and a sin synchronous detection circuit 306 via a high-frequency amplifier 303 and a phase shift circuit 304. A cos component (X component) and a sin component (Y component) of the detection signal are taken out by the synchronous detector. Here, the phase shift circuit 304 forms two signals of an in-phase component (0°) and an orthogonal component (90°) of the signal source 203 from an oscillation signal formed by the signal source 203. These signals are introduced into the cos synchronous detection circuit 305 and the sin synchronous detection circuit 306 respectively to perform the synchronous detection described above.

Unnecessary high-frequency components which are not lower than the frequency of the signal component, for example, high-frequency components of 5 KHz or more are removed from the synchronously-detected signals by low-pass filters 307 and 308. The synchronously-detected signals are an X-component output as a cos synchronous detection output and an Y-component output as a sin synchronous detection output. The magnitude of the impedance Z $(X^2+Y^2)^{1/2}$ is obtained from the X-component output and the Y-component output by a vector calculation circuit 309. Furthermore, a phase output ($\theta=\tan^{-1}Y/X$) is likewise obtained from the X-component output and the Y-component output by a vector calculation circuit ($\theta$ processing circuit) 310. Here, these filters are provided to remove noise components of the sensor signal, and cut-off frequencies corresponding to various kinds of filters are set in the filters.

Next, points (coordinate values (X, Y)) on the impedance plane coordinate system which correspond to impedances obtained according to different distances between the polishing target 102 and the eddy current sensor 210 form different circles. The respective centers of the different circles are located on the same straight line (second straight line). A first point is one point common to the different circles. These points will be described.

The following expressions are satisfied for the sensor side circuit and the conductive film side circuit shown in FIG. 3, respectively.

$$R_1 I_1 + L_1 dI_1/dt + M dI_2/dt = E \quad (1)$$

$$R_2 I_2 + L_2 dI_2/dt + M dI_1/dt = 0 \quad (2)$$

Here, M represents mutual inductance, $R_1$ represents the equivalent resistance of the sensor side circuit, and $L_1$ represents the self-inductance of the sensor side circuit. $R_2$ represents the equivalent resistance of the conductive film in which eddy current is induced, and $L_2$ represents the self-inductance of the conductive film in which eddy current flows.

Here, when $I_n = A_n e^{j\omega t}$ (sine wave) is set, the above expressions (1) and (2) are represented as follows.

$$(R_1 + j\omega L_1)I_1 + j\omega M I_2 = E \tag{3}$$

$$(R_2 + j\omega L_2)I_2 + j\omega M I_1 = 0 \tag{4}$$

From these expressions (3) and (4), the following expression (5) is derived.

$$I_1 = E(R_2 + j\omega L_2)/\{(R_1 + j\omega L_1)(R_2 + j\omega L_2) - \omega^2 M^2\} = E/\{(R_1 + j\omega L_1) + \omega^2 M^2/(R_2 j\omega L_2)\} \tag{5}$$

Accordingly, the impedance Z of the sensor side circuit is represented by the following expression (6).

$$Z = E/I_1 = \{R_1 + \omega^2 M^2 R_2/(R_2^2 + \omega^2 L_2^2)\} + j\omega\{L_1 - \omega^2 L_2 M^2/(R_2^2 + \omega^2 L_2^2)\} \tag{6}$$

Here, when a real part (resistance component) and an imaginary part (induction reactance component) of Z are represented by X and Y, respectively, the expression (6) is represented as follows.

$$Z = X + j\omega Y \tag{7}$$

Here, when $R_x = \omega^2 L_2 M^2/(R_2^2 + \omega^2 L_2^2)$ is introduced, the expression (7) is represented as follows.

$$X + j\omega Y = [R_1 + R_2 R_x] + j\omega[L_1 L_2 R_x]$$

Accordingly, $X = R_1 + R_2 R_x$, and $Y = \omega[L_1 - L_2 R_x]$, and by solving X and Y for $R_2$, $L_2$, $$R_2 = \omega^2(X - R_1)M^2/((\omega L_1 - Y)^2 + (X - R_1)^2) \tag{8}$$

$$L_2 = \omega(\omega L_1 - Y)M^2/((\omega L_1 - Y)^2 + (X - R_1)^2) \tag{9}$$

Figure 7:
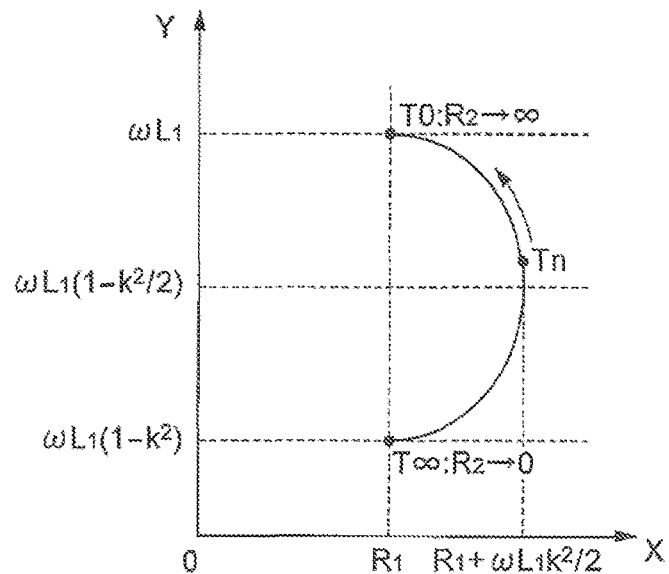
FIG. 7 is a graph showing a circular locus of a resistance component (X) and a reactance component (Y) on an impedance coordinate plane with variation of the thickness of a conductive film.

A character k shown in FIG. 7 represents a coupling coefficient, and the following relational expression (10) is satisfied.

$$M = k(L_1 L_2)^{1/2} \tag{10}$$

By applying this relational expression to (9), $$(X - R_1)^2 + (Y - \omega(1 - (k^2/2))L_1)^2 = (\omega L_1 k^2/2)^2 \tag{11}$$

This represents an equation for a circle, and X and Y form a circle, that is, the impedance Z forms a circle.

The eddy current sensor 210 outputs the resistance component X and the induction reactance component Y of the impedance of the electrical circuit containing the coils of the eddy current sensor 210. The resistance component X and the induction reactance component Y are film thickness signals reflecting the film thickness, and thus they vary according to the thickness of the conductive film on the substrate.

FIG. 7 is a diagram showing a graph which is drawn by plotting X and Y varying with the thickness of the conductive film on the XY coordinate system. The coordinate of a point T∞ is (X, Y) when the film thickness is infinite, that is, $R_2$ is equal to zero. The coordinate of a point T0 (first point) is (X, Y) when the film thickness is equal to zero on the condition that the conductance of the substrate is negligible, that is, $R_2$ is infinite. A point Tn (second point) positioned based on the values of X and Y travels to the point T0 according to decrease of the thickness of the conductive film while drawing an arcuate locus.

Figure 8:
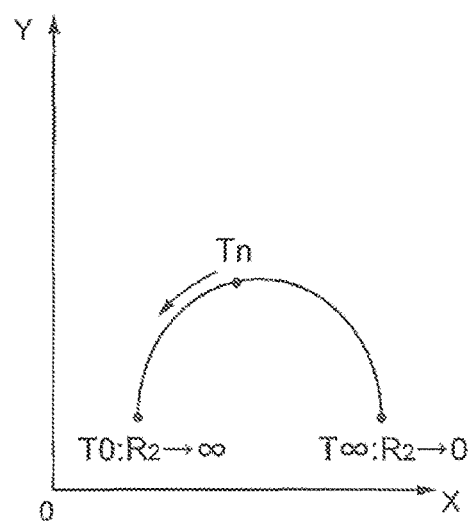
FIG. 8 is a graph obtained by rotating the graph figure of FIG. 7 counterclockwisely by 90° and further translating the resulting graph figure.

FIG. 8 is a diagram showing a graph obtained by rotating the graph figure of FIG. 7 counterclockwisely by 90° and further translating the resulting graph figure. As shown in FIG. 8, a point Tn which is positioned from the values of X and Y travels to the point T0 according to decrease of the film thickness while drawing an arcuate locus.

The coupling coefficient k represents a rate at which magnetic field generated by one coil is transferred to the other coil. The maximum value of k is equal to 1, and when the distance between the coils is larger, that is, when the thickness of the polishing pad 108 increases, k decreases.

Figure 9:
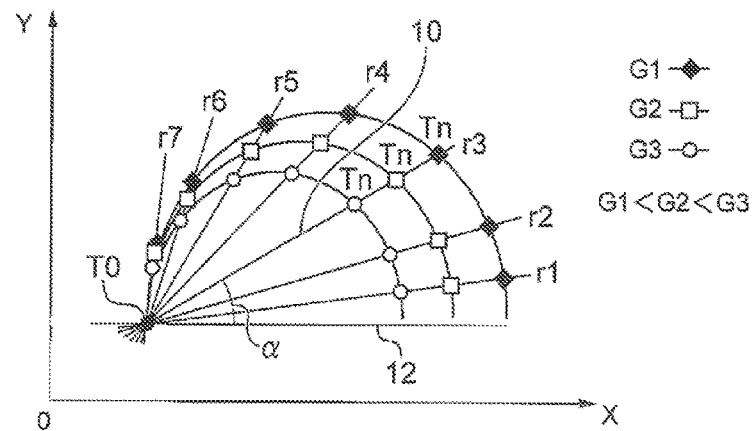
FIG. 9 is a graph showing variations of an arcuate locus of the coordinate (X, Y) according to the distance equivalent to the thickness of a polishing pad being used.

The distance G between the coil of the eddy current sensor 210 and the substrate W varies according to the thickness of the polishing pad 108 interposed therebetween. As a result, the arcuate locus of the coordinate (X, Y) varies according to the distance G (G1 to G3) corresponding to the thickness of the polishing pad 108 to be used as shown in FIG. 9. As is apparent from FIG. 9, when the coordinates (X, Y) for respective distances G between the coil and the polishing target 102 in the case of the same film thickness are connected to one another by a straight line (hereinafter referred to as "equal film thickness straight line" (first straight line)), the equal film thickness straight lines intersect to one another at the cross-point P irrespective of the distance G between the coil and the polishing target 102. This point P corresponds to the first point T0. This equal film thickness straight line rn (n: 1, 2, 3, . . . ) inclines at an angular degree α corresponding to the thickness of the conductive film (polishing target 102) with respect to a diameter (second straight line) 12 of a circle passing through the first point in FIG. 9. The diameters (second straight lines) of circles passing through the first point are identical to one another irrespective of the distance G.

The angular degree α is defined as the angular degree of the intersection angle between the diameter of a circle passing through the first point (T0) and a first straight line connecting the first point (T0) corresponding to the impedance for the film thickness of zero and a second point (Tn) corresponding to the impedance for a non-zero film thickness. When the thickness of the conductive film is the same, the angular degree α is the same irrespective of the difference in thickness of the polishing pad 108. This point will be described with reference to FIG. 10.

Figure 10:
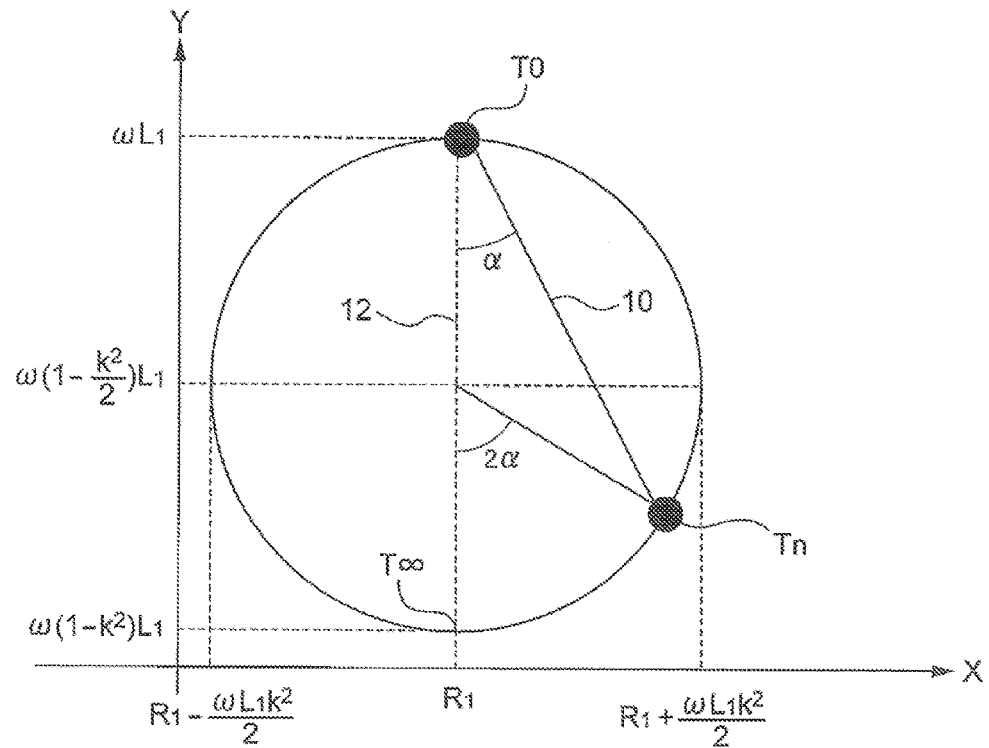
FIG. 10 is a diagram showing that an angle α is unchangeable irrespective of the thickness of the polishing pad 108.

The coordinate (X, Y) at the point Tn is represented by using the angular degree α shown in FIG. 10. From FIG. 10, $$X = R_1 + \omega(k^2/2)L_1 \sin \alpha \tag{12}$$

$$Y = \omega(1 - (k^2/2))L_1 - \omega(k^2/2)L_1 \cos \alpha \tag{13}$$

from the expressions (8) and (9) described above, $$R_2/L_2 = \omega(X - R_1)/(\omega L_1 - Y)$$

and by substituting the expressions (12) and (13) into the above expression, $$R_2/L_2 = \omega \sin 2\alpha/(1 + \cos 2\alpha) = \omega \tan \alpha \tag{14}$$

Since $R_2/L_2$ is dependent on only the film thickness and is not dependent on the coupling coefficient k, $R_2/L_2$ is not dependent on the distance between the eddy current sensor 210 and the polishing target 102, that is, the thickness of the polishing pad 108. $R_2/L_2$ is dependent on only the film thickness, and thus the angular degree α is dependent on only the film thickness. A film thickness calculator calculates the tangent of the angular angle α, and calculates the film thickness from the tangent by using the relationship of the expression (14).

A method of calculating the angular degree α and a method of calculating the film thickness will be described. In the film thickness measuring device 230 shown in FIG. 1, when eddy current formable in the polishing target 102 is detected as an impedance by the eddy current sensor 210 to measure the film thickness of the polishing target, the impedance is input from the receiver 232. The film thickness is determined from the input impedance. The film thickness measuring device 230 includes an angle calculator 234 and a film thickness calculator 238.

The angle calculator 234 calculates the angular degree $\alpha$ of an intersection angle between a first straight line 10 connecting a first point T0 corresponding to an impedance for the film thickness zero and a second point Tn corresponding to an impedance for non-zero film thickness and a diameter 12 of a circle passing through the first point T0. The film thickness calculator 238 calculates the tangent of the angular angle $\alpha$, and the film thickness is calculated from the tangent.

Figure 11:
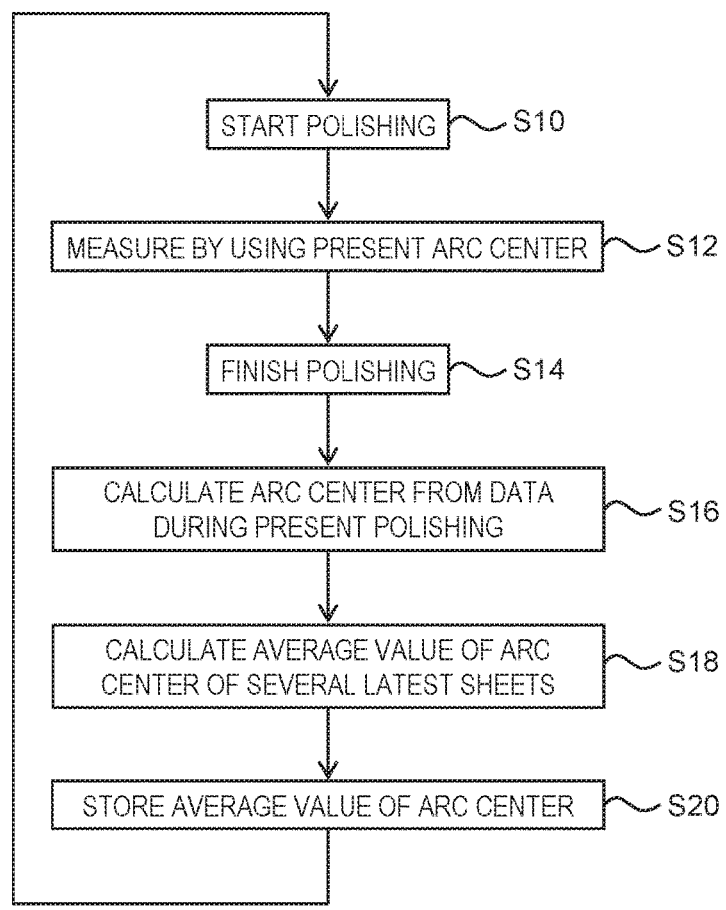
FIG. 11 is a flowchart showing a manner of determining the center of an arc.

The film thickness measuring device 230 has a first storage unit 236 capable of storing the position of the center of a circle which can be calculated from plural second points Tn on the circle obtained by the eddy current sensor 210. The first storage unit 236 has also stored information (coordinate value) on the first point T0 which has been measured and obtained in advance. When the polishing target 102 such as a wafer is polished, the impedance describes a part of a semicircle, and thus the center of an arc is calculated from plural second points Tn on the semicircle. When the center point of the arc is used to calculate the angular degree $\alpha$, the radius of the arc varies in inverse proportion to the distance between the eddy current sensor 210 and the polishing pad 108 as described above. Therefore, when the polishing processing is continued, the polishing pad 108 is worn out and the radius of the arc increases. According to the increase of the radius of the arc, it is necessary to shift the center of the arc. A specific manner of determining the arc center is shown in FIG. 11. Upon start of polishing (step S10), the film thickness is measured by the angle calculator 234 and the film thickness calculator 238 as described later by using a present arc center which has been stored in the first storage unit 236 (step S12).

When the polishing is finished (step S14), a center calculator 237 calculates an arc center from data obtained during the present polishing operation based on the impedance input from the receiver 232 to the center calculator 237 during the measurement (step S16). The details will be described later. The center calculator 237 calculates the average value of the arc center of the latest several polishing targets 102, thus obtained (step S18). The calculated average value of the arc center is stored in the first storage unit 236 (step S20). Returning to step S10, polishing of a next polishing target 102 is started. When a first polishing pad 108 is polished, the first storage unit 236 does not have any data associated with polishing. At that time, a test wafer is polished in advance to create data.

By updating the data of the arc center as described above, the variation of the arc center caused by wear-out of the polishing pad 108 can be followed. Furthermore, when the polishing pad 108 is exchanged or when the polishing pad 108 is rapidly worn away due to break-in processing (dresser processing for removing clogging of the polishing pad 108 or the like), the polishing apparatus controller 140 detects this operation. Then, a test wafer is polished to determine and store an arc center again. At this time, averaging for the latest several polishing targets is not performed.

Figure 12:
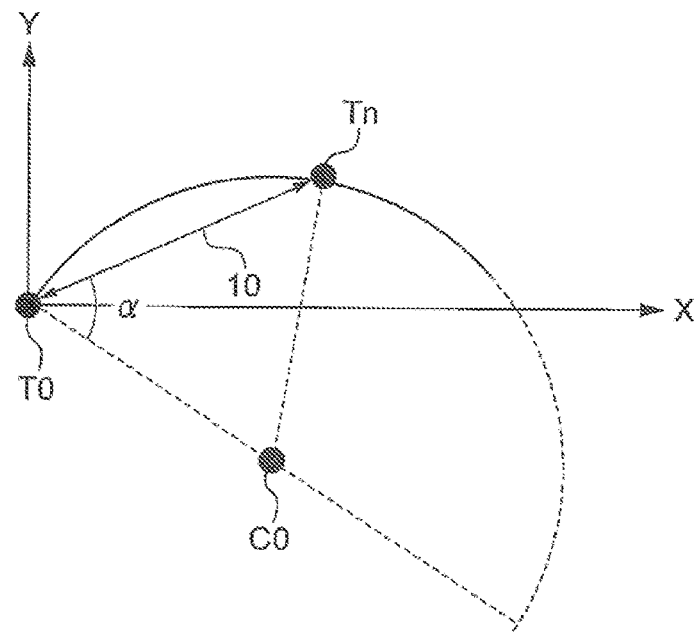
FIG. 12 is a diagram showing a manner of calculating the angle α.

As shown in FIG. 12, the angle calculator 234 calculates the tangent from the coordinate value of the position of the center C0 of a circle stored in the first storage unit 236, the coordinate value of the first point T0 stored in the first storage unit 236 and the coordinate value of the second point Tn obtained by the eddy current sensor 210 after the position of the center of the circle is calculated. The calculation expression is as follows, for example.

An equation $ax+by=e$ for a straight line passing through the center C0 and the first point T0 is calculated from the coordinate value of the center C0 and the coordinate value of the first point T0. An equation $cx+dy=f$ for a straight line passing through the second point Tn and the first point T0 is calculated from the coordinate value of the second point Tn and the coordinate value of the first point T0. At this time, the angular degree $\alpha$ between the two straight lines satisfies $\cos \alpha = \sqrt{((ac+bd)^2)/(\sqrt{(a^2+b^2)}\sqrt{(c^2+d^2)})}$. When the $\cos \alpha$ is determined, the tangent can be calculated from the following expression.

$$\tan \alpha = 1/(1-(\cos \alpha)^2)/\cos \alpha$$

In this embodiment, the tangent is directly determined without determining the angular degree $\alpha$. However, the tangent may be determined after the angular degree $\alpha$ is determined. For example, the following method may be used as a method of determining the angular degree $\alpha$. The angular degree $\alpha$ is determined by calculating $\cos \alpha$ as described above and then calculating arccosine of $\cos \alpha$.

In this embodiment, the tangent is directly determined and then the film thickness is determined. However, the film thickness may be directly determined from the angular degree $\alpha$. The relationship between the angular degree $\alpha$ and the film thickness for different thicknesses of the polishing pad 108 is clarified according to this embodiment. Therefore, the relationship between the angular degree $\alpha$ and the film thickness can be achieved by merely performing the measurement at a smaller frequency than the prior art in advance. That is, the relationship between the angular degree $\alpha$ and the film thickness can be achieved by merely performing the measurement for about three film thicknesses of the polishing target 102 in advance, for one distance between the eddy current sensor 210 and the polishing target 102 (that is, one thickness for the polishing pad 108). By using the relationship between the angular degree $\alpha$ and the film thickness as described above, the film thickness can be directly determined from the angular degree $\alpha$. In this case, there is an advantage that it is sufficient only to perform the measurement at a smaller frequency than the prior art in advance.

Figure 13:
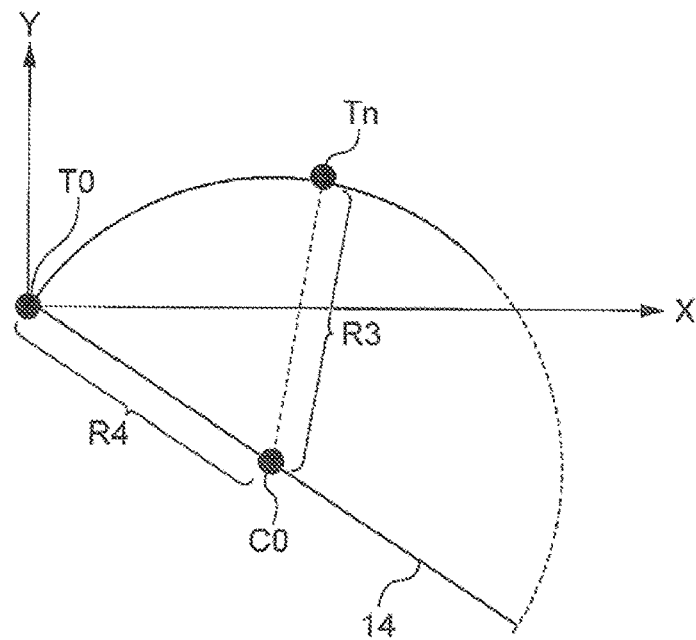
FIG. 13 is a diagram showing another manner of calculating the angle α.

Another embodiment different from the embodiment shown in FIG. 12 will be described with reference to FIG. 13. As described above, the center point of an arc is located on a fixed approximate straight line when the distance between the eddy current sensor 210 and the polishing target 102 varies. Therefore, calibration is performed on the output of the eddy current sensor 210 in advance, and impedance data are achieved while the distance between the eddy current sensor 210 and the polishing target 102 is varied, thereby achieving an arc center approximate straight line in advance. When the arc center approximate straight line is predetermined, a point on the approximate straight line which is located at the same distance from both the second point Tn and the first point T0 corresponds to the arc center point, so that the center point can be immediately determined at the time of the measurement. This method will be described with reference to FIG. 13.

In this method, points on the coordinate system which correspond to impedances obtained for different distances between the polishing target 102 and the eddy current sensor 210 form different circles, and the center of each of the different circles is located on a second straight line 14. The second straight line 14 corresponds to the diameter 12 described above. The film thickness measuring device 230 has a second storage unit (not shown) capable of storing information of the second straight line 14. The angle calculator determines that a point which is located on the second straight line stored in the second storage unit and at which the distance R4 from the first point T0 and the distance R3 from the second point Tn are equal to each other is the center C0 of a circle to which the second point Tn belongs. The angular degree α is calculated from the position of the center C0 of the circle, the first point T0 and the second point Tn according to the method described with reference to FIG. 12. The point on the second straight line 14 which satisfies R3=R4 is the present arc center C0.

Figure 14:
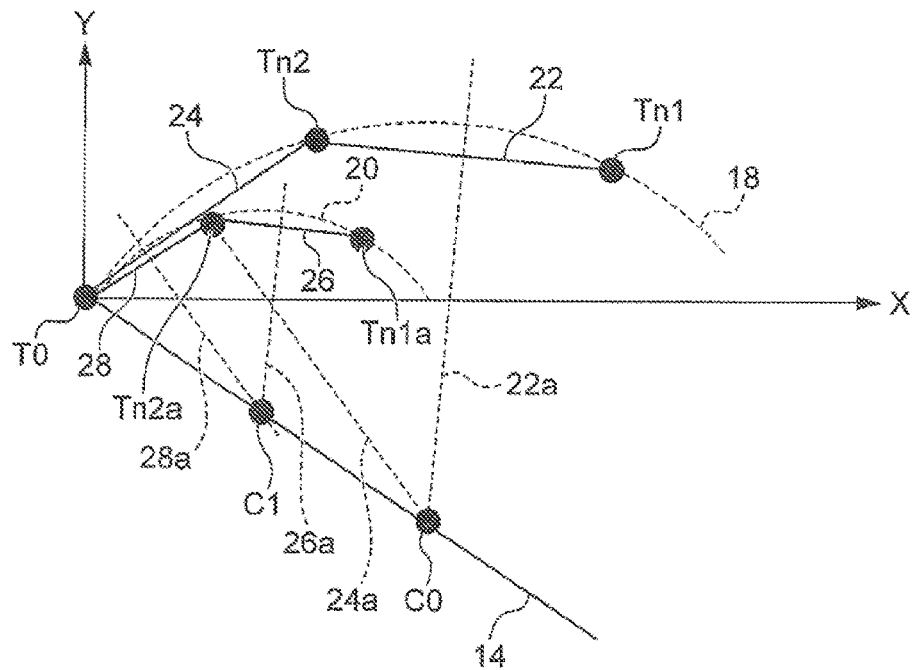
FIG. 14 is a diagram showing a manner of determining a second straight line 14.

A method of determining the second straight line 14 will be described with reference to FIG. 14. The film thickness measuring device 230 has a straight line calculator (not shown) for calculating information on the second straight line. With respect to each of at least two circles corresponding to the different distances between the polishing target 102 and the eddy current sensor 210, the straight line calculator calculates the center C0, C1 of each circle from at least three points on the circle. Information on a straight line connecting the calculated centers C0 and C1 of the at least two circles is output as the information on the second straight line to the second storage unit. The information on the second straight information contains the gradient of the straight line, the coordinate value of at least one point on the straight line, coefficients of the equation of the straight line, etc. The second storage unit stores the input information on the second straight line 14.

Specifically, data on circles 18 and 20 are achieved with two or more kinds of calibration wafers having different thicknesses by the eddy current sensor 210. Data on the circle 18 are set to data at points Tn1 and Tn2. With respect to the circle 18, data at three or more points containing the first point T0 are achieved, and thus a point C0 at which bisectors 22a and 24a of lines 22 and 24 connecting the respective points intersect to each other corresponds to the arc center of the circle 18. The same is applied to the circle 20. That is, data on the circle 20 are set to data at points Tn1a and Tn2a. With respect to the circle 20, data at three or more points containing the first point T0 are achieved, and thus a point C1 at which bisectors 26a and 28a of lines 26 and 28 connecting the respective points intersect to each other corresponds to the arc center of the circle 20. When this operation is performed for different distances between two or more types of polishing targets 102 and the eddy current sensor 210, the arc centers C0 and C1 at the two or more points are determined, and an approximate straight line connecting these arc centers may be determined.

The straight line calculator may adopt another method of achieving the information on the second straight information. That is, it is possible to determine the second straight line 14 from the distance between one type polishing target 102 and the eddy current sensor 210. That is, with respect to one circle, the center of the circle is determined from at least three points on the circle, and information on a straight line connecting the calculated center of the circle and the first point T0 may be output as the information on the second straight line to the second storage unit. The second storage unit stores the input information of the second straight line.

This method utilizes the fact that a straight line is determined from two points. A straight line connecting the arc center C0 of the distance between one kind of polishing target 102 and the eddy current sensor 210 and the first point T0 may be set as an approximate straight line of the arc center.

Figure 15:
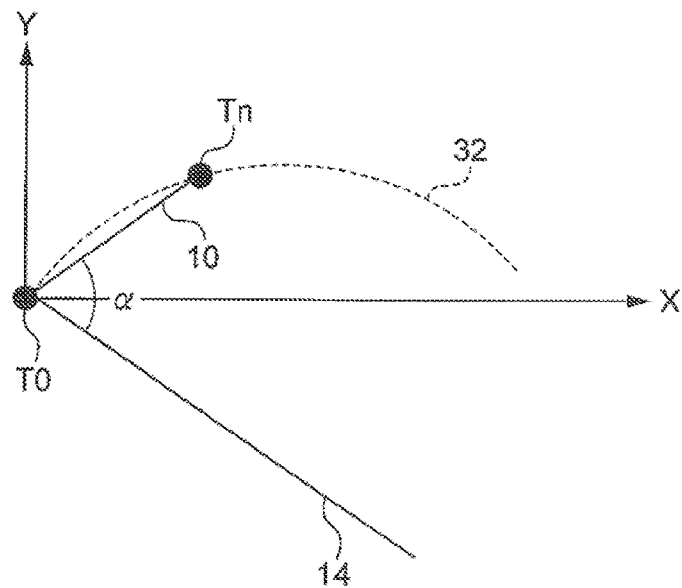
FIG. 15 is a diagram showing a manner of calculating the angle α without using the center of an arc.

The angular degree α calculating method which has been described is based on use of the arc center. However, it is possible to use a method which does not use the arc center. A method which does not use the arc center will be described with reference to FIG. 15. In FIG. 15, the arc center is not determined, but the intersection angular degree α between the straight line 10 connecting the first point T0 and the second point Tn and the second straight line 14 as an arc center approximate straight line is determined. According to this method, the angle calculator calculates the angular degree of the intersection angle between the stored second straight line 14 and the first straight line 10 as the angular degree α of the intersection angle between the first straight line 10 and a diameter of a circle 32 which passes through the first point T0.

As is apparent from FIGS. 9 and 12, etc., the second straight line 14 (the diameter of a circle) may be parallel or vertical to the X-axis or Y-axis, and may be neither parallel nor vertical to the X-axis and the Y-axis. The position and direction of the second straight line 14 (the diameter of the circle) may be set to be dependent on the setting of a measurement system or a processing system or conformed with user's demand of the apparatus.

Any method other than the above-described method may be adopted as the calculation method of the angular degree α insofar as the value of the angular degree α can be calculated.

Next, the film thickness calculator 238 for calculating the film thickness from the tangent will be described. This embodiment utilizes the relationship between the reciprocal of the tangent and the film thickness. First, the relationship between the reciprocal of the tangent and the film thickness will be described.

The relationship of the expression (14) described above, that is, the following expression is satisfied between the tangent and the resistance value of the metal film.

$$R_2/L_2 = \omega \tan \alpha \quad (14)$$

Here, $R_2$ represents the resistance value of the metal film. Accordingly, $R_2$ and $\tan \alpha$ are in proportion to each other. Furthermore, $R_2$ and the film thickness have the following relationship.

$$R_2 = \rho L/tW \quad (15)$$

Here, ρ represents resistivity, L, W represent the length and width of the metal film respectively, and t represents the film thickness. From the expressions (14) and (15), it is known that the film thickness t and the angular degree α have the following relationship: $R_2 \propto (1/t) \propto \omega \tan \alpha$, that is, $1/\tan \alpha \propto t$.

Figure 16:
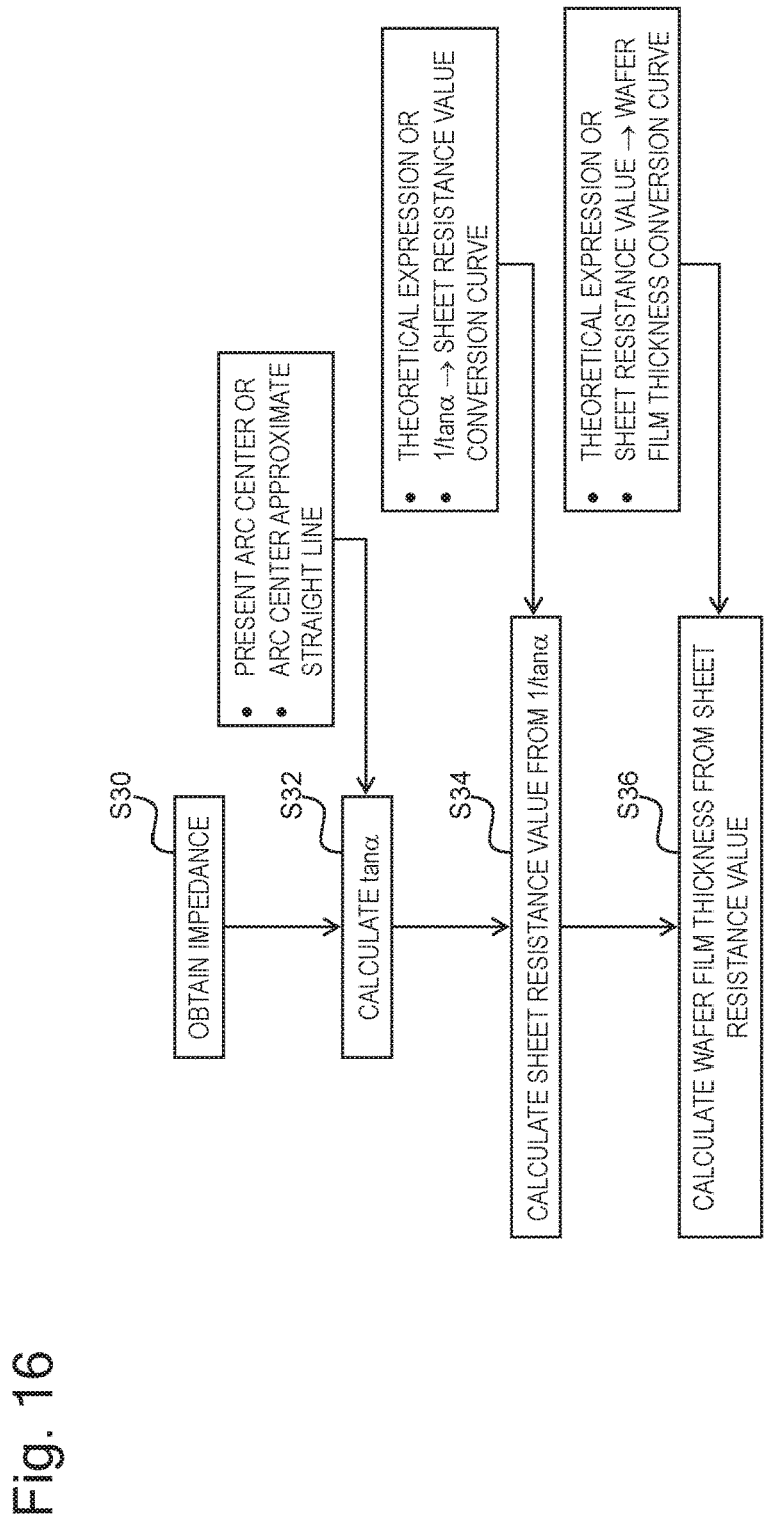
FIG. 16 is a flowchart showing the whole of a method of calculating the film thickness.

Accordingly, $1/\tan \alpha$ and the film thickness t are in proportion to each other. However, when the film thickness is reduced, the expression (15) may not be satisfied according to the kind of metal. On the other hand, the expression (14) is satisfied at all times. Therefore, in this embodiment, with respect to a method of calculating $R_2$ as a sheet resistance value from $1/\tan \alpha$, the method is determined by using an approximate curve representing the relationship between $1/\tan \alpha$ and the sheet resistance value which is obtained by prior calibration. Subsequently, with respect to the conversion from the sheet resistance value to the metal film thickness, a conversion method is determined by using an approximate curve representing the relationship between the sheet resistance value and the metal film thickness which is obtained by prior calibration. The film thickness calculating method performed as described above is shown in FIG. 16.

First, a resistance component (X) and a reactance component (Y) on the impedance coordinate plane are achieved by the eddy current sensor 210 and the receiver 232 (step S30). Subsequently, in the angle calculator 234, tan α is calculated by one of the two methods described above, that is, the method using the present arc center or the method using the arc center approximate straight line (step S32). In the film thickness calculator 238, the sheet resistance value is calculated from 1/tan α (step S34). In this case, a theoretical expression representing the relationship between 1/tan α and the sheet resistance value or a curve obtained by the prior calibration for converting 1/tan α to the sheet resistance value is used. The wafer film thickness is calculated from the thus-obtained sheet resistance value (step S36). At this time, a theoretical expression representing the relationship between the sheet resistance value and the wafer film thickness or a curve obtained by prior calibration for converting the sheet resistance value to a wafer film thickness is used.

The method of determining the film thickness from 1/tan α according to this embodiment has the following advantage.

(1) In Japanese Patent Laid-Open No. 2005-121616, the reference point (the first point T0 of this embodiment) is determined in advance by multiple measurements. That is, impedances have been obtained in advance for various film thicknesses and distances between plural kinds of polishing targets 102 and the eddy current sensor 210. This embodiment does not require to perform multiple measurements as described above. When the measurement frequency is required to be minimized, only by determining the first point T0 for the thickness of one type polishing pad 108, variation of the measurement value which is caused by the thickness of the polishing pad 108 can be considered.

(2) Since 1/tan α and 1/$R_2$ have linear characteristics, it can be possible to measure the sheet resistance value and the film thickness.

(3) The length of the first straight line 10 shown in FIG. 10, etc. represents the magnitude of the impedance, and the magnitude of the impedance may be considered as the energy of eddy current. It is possible in this embodiment to determine the length of the first straight line 10. By regarding decrease of the measurement value of the eddy current sensor 210 at the edge of the polishing target 102 as decrease of the energy, the decrease of the energy can be corrected. Accordingly, a range in which the film thickness measurement at the edge can be performed can be expanded to the end portion. In this embodiment, such edge correction can be used.

The examples of the embodiments of the present invention have been described above. The foregoing embodiments of the present invention are provided to make the understanding of the present invention easy, and do not limit the present invention. The present invention can be modified and improved without departing from the subject matter of the present invention, and contains equivalents thereto. In a range where at least a part of the foregoing problem can be solved or in a range where at least a part of the effect can be achieved, it is possible to make any combination or eliminate the respective constituent elements described in the claims and the specification.

This application claims priority under the Paris Convention to Japanese Patent Application No. 2016-138434 filed on Jul. 13, 2016. The entire disclosure of Japanese Patent Laid-Open No. 2005-121616 including specification, claims, drawings and summary is incorporated herein by reference in its entirety.

REFERENCE SIGNS LIST

T0 first point
m equal film thickness straight line
R1 distance
R2 distance
10 first straight line
14 second straight line
100 polishing apparatus
102 polishing target
108 polishing pad
210 eddy current sensor
230 film thickness measuring device
232 receiver
234 angle calculator
236 first storage unit
238 film thickness calculator

What is claimed is:

1. A film thickness measuring device for measuring a film thickness of a polishing target wherein when eddy current formable in the polishing target is detected as an impedance by an eddy current sensor, the film thickness measuring device receives an input of the impedance and determines the film thickness from the input impedance, wherein when respective axes of a coordinate system having two orthogonal coordinate axes are associated with a resistance component and a reactance component of the impedance respectively, a point on the coordinate system which corresponds to the impedance forms at least a part of a circle, and wherein the film thickness measuring device comprises:

an angle calculator that calculates a tangent or angular degree of an intersection angle between a first straight line connecting a first point corresponding to the impedance for a film thickness of zero and a second point corresponding to the impedance for a non-zero film thickness and a diameter of the circle which passes through the first point; and a film thickness calculator that determines the film thickness from the tangent or the angular degree.

2. The film thickness measuring device according to claim 1, further comprising a first storage unit capable of storing a center position of the circle that can be calculated from a plurality of the second points located on the circle and obtained by the eddy current sensor, wherein the angle calculator calculates the tangent or the angular degree from the stored center position of the circle, the first point and the second points obtained by the eddy current sensor after the center position of the circle is calculated.

3. The film thickness measuring device according to claim 1, wherein points on the coordinate system that correspond to impedances obtained for different distances between the polishing target and the eddy current sensor form different circles, center of each of the different circles being located on a second straight line, and wherein the film thickness measuring device further comprises a second storage unit capable of storing information on the second straight line, and the angle calculator determines that a point which is located on the stored second straight line and at which a distance from the first point and a distance from the second point are equal to each other is a center of the circle to which the second point belongs, and calculates the tangent or the angular degree from the position of the center of the circle, the first point and the second point.

4. The film thickness measuring device according to claim 1, wherein points on the coordinate system that correspond to impedances obtained for different distances between the polishing target and the eddy current sensor form the different circles, center of each of the different circles being located on a second straight line and the first point being located on the second straight line, and wherein the film thickness measuring device has a second storage unit capable of storing information on the second straight line, and the angle calculator calculates the tangent or the angular degree while the angular degree of an intersection angle between the stored second straight line and the first straight line is set as the angular degree of the intersection angle between the first straight line and the diameter of the circle that passes through the first point.

5. The film thickness measuring device according to claim 3, further comprising a straight line calculator that calculates information on the second straight line, wherein with respect to each of the at least two circles corresponding to different distances between the polishing target and the eddy current sensor, the straight line calculator calculates a center of each of the circles from at least three points on the circle, and outputs information on a straight line connecting the calculated centers of the at least two circles as information on the second straight line to the second storage unit, and the second storage unit stores the input information on the second straight line.

6. The film thickness measuring device according to claim 3, wherein points on the coordinate system that correspond to impedances obtained for different distances between the polishing target and the eddy current sensor form the different circles, and the first point is a point common to the different circles, and wherein the film thickness measuring device has a straight line calculator that calculates information on the second straight line, with respect to one of the circles, the straight line calculator calculates a center of the circle from at least three points on the circle, and outputs information of a straight line connecting the calculated center of the circle and the first point as information on the second straight line to the second storage unit, and the second storage unit stores the input information on the second straight line.

7. A polishing apparatus for polishing a polishing target comprising:
   a polishing unit that polishes the polishing target;
   an eddy current sensor that forms eddy current in the polishing target and detect the formed eddy current to measure a film thickness of the polishing target;
   a receiver for outputting the detected eddy current as an impedance; and
   the film thickness measuring device according to claim 1 that receives an input of the impedance and determines the film thickness from the input impedance.

8. A film thickness measuring method for measuring a film thickness of a polishing target by, when eddy current formable in the polishing target is detected as an impedance by an eddy current sensor, receiving an input of the impedance and determining the film thickness from the input impedance, wherein when respective axes of a coordinate system having two orthogonal coordinate axes are associated with a resistance component and a reactance component of the impedance respectively, a point on the coordinate system which corresponds to the impedance forms at least a part of a circle, and
   wherein the film thickness measuring method comprises:
      a step of calculating a tangent or angular degree of an intersection angle between a first straight line connecting a first point corresponding to the impedance for a film thickness of zero and a second point corresponding to the impedance for a non-zero film thickness and a diameter of the circle which passes through the first point; and
      a step of determining the film thickness from the tangent or the angular degree.

9. A polishing method for polishing a polishing target comprising:
   a polishing step of polishing the polishing target;
      a step of forming eddy current in the polishing target and detecting the formed eddy current to measure a film thickness of the polishing target;
      a step of outputting the detected eddy current as an impedance; and
      a film thickness measuring step of receiving an input of the impedance and determining the film thickness from the input impedance,
   wherein when respective axes of a coordinate system having two orthogonal coordinate axes are associated with a resistance component and a reactance component of the impedance respectively, a point on the coordinate system which corresponds to the impedance forms at least a part of a circle, and
   wherein the film thickness measuring step comprises:
      a step of calculating a tangent or angular degree of an intersection angle between a first straight line connecting a first point corresponding to the impedance for a film thickness of zero and a second point corresponding to the impedance for a non-zero film thickness and a diameter of the circle which passes through the first point; and
      a step of determining the film thickness from the tangent or the angular degree.

* * * * *